United States Patent
Hegazi

(10) Patent No.: US 7,560,711 B2
(45) Date of Patent: Jul. 14, 2009

(54) MULTIPLE FINGERPRINTING OF PETROLEUM OILS USING NORMALIZED TIME-RESOLVED LASER-INDUCED FLUORESCENCE SPECTRAL SUBTRACTIONS

(75) Inventor: Ezzat M. Hegazi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 11/463,322

(22) Filed: Aug. 9, 2006

(65) Prior Publication Data

US 2008/0035858 A1   Feb. 14, 2008

(51) Int. Cl.
G01N 21/64 (2006.01)
(52) U.S. Cl. .................. 250/461.1; 250/459.1
(58) Field of Classification Search .......... 250/461.1, 250/459.1
See application file for complete search history.

(56) References Cited

U.S. PATENT DOCUMENTS

| | | | |
|---|---|---|---|
| 5,049,738 A * | 9/1991 | Gergely et al. ........... 250/301 |
| 5,674,698 A | 10/1997 | Zarling et al. |
| 5,686,310 A | 11/1997 | Haystead et al. |
| 5,990,484 A * | 11/1999 | Ohsuka ................. 250/458.1 |
| 6,272,376 B1 | 8/2001 | Marcu et al. |
| 6,633,043 B2 * | 10/2003 | Hegazi et al. .......... 250/461.1 |
| 7,387,891 B2 * | 6/2008 | Boege et al. .......... 435/288.7 |
| 2002/0121611 A1 * | 9/2002 | Yokokawa et al. ...... 250/458.1 |
| 2004/0248144 A1 | 12/2004 | Mir |
| 2008/0040044 A1 * | 2/2008 | Dunlay et al. .......... 702/19 |
| 2009/0032736 A1 * | 2/2009 | Tanaami ............... 250/459.1 |

OTHER PUBLICATIONS

Alan G. Ryder; "Quantitative Analysis of Crude Oils by Fluorescence Lifetime and Steady State Measurements using 380-nm Excitation"; 2002 Society for Applied Spectroscopy; vol. 56, No. 1, 2002; pp. 107-116; Department of Physics, National University of Ireland-Galway, Galway, Ireland.

Garon C. Smith et al.; "The Red-Shift Cascade: Investigations into the Concentration-Dependent Wavelength Shifts in Three-Dimensional Fluorescence Spectra of Petroleum Samples"; Department of Chemistry, University of Montana, Missoula Montana 59812 (G.S.); and Department of Chemistry, Bellarmine College, 2001 Newberg Road, Louisville, Kentucky 40205 (J.F.S.).

(Continued)

*Primary Examiner*—David P Porta
*Assistant Examiner*—Jessica L Eley
(74) *Attorney, Agent, or Firm*—Lowe Hauptman Ham & Berner, LLP

(57) ABSTRACT

A method based on spectral subtractions of normalized time-resolved laser-induced fluorescence (TRLIF) spectra produces multiple fingerprints of petroleum oils simultaneously. The method utilizes the simultaneous excitation of the TRLIF spectra of six oil samples using synchronized optical shutters. Five of the samples are standard oil samples while the sixth is the targeted sample. Instead of one fingerprint for the targeted sample, the technique produces multiple fingerprints representing the spectral subtractions between the normalized TRLIF spectra of the target sample and those of each of the standard oil samples. The technique provides fingerprints of higher distinguishing ability than a prior method, allowing it to discriminate between closely similar petroleum oils even under weathered conditions. The technique requires no sample preparation and can be applied remotely. It can also identify the original grade of the petroleum oils from their weathered remains.

14 Claims, 13 Drawing Sheets

OTHER PUBLICATIONS

J. B. F. Lloyd; "Partly Quenched, Synchronously Excited Fluorescence Emission Spectra in the Characterisation of Complex Mixtures"; Analyst, Nov. 1974, vol. 99, pp. 729-738; West Midland Forensic Laboratory, Priory House, Gooch Street North, Birmingham, B5 6QQ.

J. B. F. Lloyd; "The Nature and Evidential Value of the Luminescence of Automobile Engine Oils and Related Materials"; Part III. Separated Luminescence; J. Forens. Sci. Soc. (1971), 11, 235; Home Office Forensic Science Laboratory, Priory House, Gooch Street North, Birmingham 5, England.

Paolo Camagni et al.; "Diagnostics of Oils Pollution by Laser-Induced Fluorescence"; IEEE Transactions on Geoscience and Remote Sensing. vol. GE-26, No. 1, Jan. 1988.

Digambara Patra et al.; "Study of diesel fuel contamination by excitation emission matrix spectral subtraction fluorescence"; Analytica Chimica Acta 454 (2002) 209-215; Department of Chemistry, Indian Institute of Technology Madras, Chennai 600036, India.

Digambara Patra et al.; "Excitation Emission Matrix Spectral Subtraction Fluorescence to Check Adulteration of Petrol by Kerosene"; Applied Spectroscopy; vol. 55, No. 3, 2001; Department of Chemistry, Indian Institute of Technology Madras, Chennai 600 036, India.

I. M. Warner et al.; "Analysis of Multicomponent Fluorescence Data"; Analytical Chemistry, vol. 49, No. 4, Apr. 1977; Department of Chemistry, University of Washington, Seattle Washington and Department of Pathology, University of Washington, Seattle Washington.

R. M. Measures et al.; "Laser Induced Fluorescent Decay Spectra- A New Form of Environmental Signature"; Optical Engineering-Nov./Dec. 1974; vol. 13-No. 6; Institute for Aerospace Studies, University of Toronto and Defense Research Board, Petawawa, Ontario, Canda.

Paolo Camagni et al.; "Fluorescence response of mineral oils: spectral yield vs absorption and decay time"; Applied Optics/vol. 30, No. 1/ Jan. 1, 1991.

M. F. Quinn et al.; "Measurement and analysis procedures for remote identification of oil spills using a laser fluorosensor"; vol. 15, pp. 2637-2658; 1994 Taylor & Francis Ltd; Kuwait Institute for Scientific Research, Safat, Kuwait and IBM/Kuwait Scientific Center, Safat, Kuwait.

E. Hegazi et al.; "Estimation of crude oil grade using time-resolved fluorescence spectra"; 2002 Elsevier Science B. V.; Laser Research Section, Center for Applied Physical Sciences Research Institute, King Fahd University of Petroleum and Minerals, Dhahran 31261, Saudi Arabia.

E. Hegazi et al.; "New Approach for Spectral Characterization of Crude Oil Using Time-Resolved Fluorescence Spectra"; vol. 55, No. 2, 2001; Applied Spectroscopy; Laser Research Section, Center for Applied Physical Sciences, Research Institute, King Fahd University for Petroleum and Minerals, Dhahran, 31262, Saudi Arabia.

* cited by examiner

MULTIPLE FINGERPRINTING OF PETROLEUM OILS USING NORMALIZED TIME-RESOLVED LASER-INDUCED FLUORESCENCE SPECTRAL SUBTRACTIONS

FIELD OF THE INVENTION

The present invention relates to LIF-UV spectroscopy and more particularly to the spectral characterization of neat and weathered petroleum oils using time-resolved fluorescence spectroscopy.

BACKGROUND OF THE INVENTION

Description of the Related Art

Because of its high sensitivity in detecting fluorescing materials, its wide tuning ability in terms of available excitation wavelengths, and the different ways it can detect and measure the resulting fluorescence, Laser-induced fluorescence (LIF) spectroscopy has found a growing interest in many fields that require element and compound identifications in gas, liquid, and solid matters. Among such fields is the characterization of petroleum oils and their derivatives.

Several fluorescence methods have been applied to the field of petroleum oils. Most notably are: (a) the Synchronous Scan Spectroscopy in which the oil spectra are produced by scanning the excitation wavelength and the emission wavelength, simultaneously, at a fixed wavelength separation. (b) The Contour (Total Luminescence) Spectroscopy in which contour diagrams for the oils are constructed out of several emission spectra that are excited at different excitation wavelengths. And (c) the Time-resolved Laser-Induced Fluorescence (TRLIF) Spectroscopy in which the characterization of the oils is done by monitoring the spectral as well as the temporal characteristics of the emitted fluorescence in either the excitation or in the detection stages or in both.

The most attractive feature of the TRLIF spectroscopy over the former two types of fluorescence spectroscopy is its suitability for remote sensing applications. This is attributed to the fact that the technique already employs Q-switched pulsed lasers of high energy pulses capable of exciting oil samples located at long distances.

The application of the TRLIF spectroscopy in oil characterization is mainly done by measuring and analyzing the resulting fluorescence lifetimes at particular emission wavelengths. De-convolving the pulse of the temporal fluorescence response from that of the laser must be taken care of in this case because of the extensive overlap of the two pulses. A different technique of TRLIF spectroscopy in oil characterization was introduced recently in which the analysis is done by measuring the TRLIF spectra at narrow time-gates within the temporal profile of the laser pulse. The resulting TRLIF spectra are then plotted in terms of contour diagrams that serve as unique fingerprints. In that technique, the constructed contour diagrams basically map the effect of the laser-pulse convolution on the TRLIF fluorescence spectra in the specific narrow time gates at which they have been measured. Thus, instead of getting rid of the convolution between the laser and the emitted fluorescence pulses the technique takes advantage of its presence so as to bring about systematic changes in the shapes of the LIF spectra. These changes depend on the composition of the petroleum oil. Hence, oils of different compositions, e.g., of different grades, will produce different sets of these systematic changes and, therefore could be discriminated from each other by simply comparing their corresponding contour maps.

The question now is what is this limit of discrimination? In other words, how different the crude petroleum oils should be so that the fingerprints produced by this technique could discriminate between them. This important point was not addressed in my previous U.S. Pat. No. 6,663,043 which is incorporated herein in its entirety by reference. In this patent, the contour diagrams were constructed by mapping the intensities of the normalized TRLIF spectra as functions of the emitted wavelength and time-gates, simultaneously. Fingerprints of this type were useful in discriminating the neat crude oils of different grades from each other and also in discriminating between the weathered oils and their corresponding neat ones. However, the discrimination ability of this type of fingerprints is not enough to distinguish between neat crude oils that are closely similar, or between crude oils, which have become weathered under conditions of seawater oil spills.

The present invention describes a technology that produces a different concept of fingerprints having much higher distinguishing ability than the previous invention. It addresses the issue of discriminating between petroleum oils that are closely similar. It also addresses the issue of discriminating between spilled petroleum oils that have been severely weathered in seawater and tracing them back to their original neat sources. This is made possible by concurrently producing, from a single laser beam, a set of multiple fingerprints for the oil sample instead of only one fingerprint. These multiple fingerprints are measured in such a way that they relate to a number of standard oil samples serving as references. The measured parameter is not the simple normalized TRLIF spectra of the targeted oil as in the previous invention, but rather the spectral subtractions of the targeted oil's TRLIF spectra relative to those of the standard oils. Comparisons between spectral subtractions provide a higher distinguishing ability than comparisons between the spectra themselves. Also the choice of the standard oils, in itself, provides another feature that could be utilized to increase the distinguishing ability of the fingerprints. The standard oils are recommended to be neat petroleum oils having a wide range of different grades, more particularly, neat oils belonging to the same geographic region from which the original type of targeted oil sample, whether neat or weathered sample, is suspected to be. However, this recommendation is for convenience only and is not a must.

In order to produce all the multiple fingerprints of the targeted oil sample concurrently the setup of the previous invention must be altered in three fundamental ways. The fundamental alterations must be in all of the three essential stages of the setup, namely, in the way the samples are excited, the way the TRLIF spectra are detected and acquired, and the way the resulting data is extracted and analyzed.

In the excitation stage, instead of a single quartz cuvette the setup here has an ensemble of six quartz cuvettes arranged parallel to each other in a linear configuration. The sixth cuvette is the one that holds the targeted oil sample, while the first five cuvettes are reserved for the standard oils. The way the six cuvettes are excited concurrently by the same laser beam is done by employing a set of five UV neutral density plates plus one 100% reflecting UV mirror, to reflect the laser beam into the five standard oil samples and the targeted sample, respectively, and six small optical shutters that allow only one cuvette to be irradiated at a time. The optical shutters are all synchronized with the laser Q-switching of the laser. In the remote sensing setup the sixth cuvette is cancelled by removing the 100% reflecting mirror to allow the laser beam to continue along its path to hit the remote target.

In the detection and data acquisition stage the setup uses six pairs of UV lenses that collect the fluorescence emission from all the cuvettes and focus them onto the slit of a monochromator. Because only one oil sample is excited at a time the monochromator is synchronized in such a way that the scanning increment from one wavelength to the next is delayed until the fluorescence emission from the six samples have all passed through. This necessitates that the monochromator be run in step mode. The data acquisition on the signal processor boxcar is, accordingly, modified to allow groups of six points instead of only single points to be digitized and temporarily stored in a single array. In this way, each resultant curve in the boxcar corresponds to a composite TRLIF spectrum, which contains intermingled data belonging to six TRLIF spectra instead of one. In the remote setup, a telescope is used in place of the sixth cuvette and a filter is installed to prevent residues of the scattered laser beam from affecting the photomultiplier.

In the data analysis stage the modification is also essential since first it has to deal with a group of six spectra instead of one and second it has to present the data in spectral subtraction forms. This is done by software developed for this purpose. Such software incorporates conventional programs and its construction is well within the ability of a person of ordinary skill in the art. In the present invention the composite TRLIF spectra makes up only a small step in the data analysis, and is only present temporarily in the signal processor. The actual output is a set of five subtracted spectra instead. The modification in this stage is the same for the non-remote and the remote setups with the exception that the spectra of the targeted oil sample must be corrected with respect to the filter response.

The present invention also contemplates a prototype of the experimental setup and demonstrates how to produce, for each targeted oil sample, a set of five fingerprints related to five standard oils. Although the prototype uses a monochromator/photomultiplier/signal-processor combination for the data acquisition stage, it can also be built using a gated ICCD system instead to produce near real-time fingerprints.

SUMMARY OF THE INVENTION

This invention contemplates a technique for producing a set of multiple fingerprints for each petroleum oil sample in a simultaneous manner. The fingerprints are constructed from spectral subtractions between normalized TRLIF spectra of a targeted oil sample and those of five different standard petroleum oils.

The fingerprints are produced (1) by exciting all of the six oil samples simultaneously by using only one laser beam. This is done by employing a set of five neutral density plates, one mirror, and a linear configuration of six optical shutters mounted on stepper motors and controlled by an electronic timer circuit. (2) By time-resolving and spectrally measuring the resulting fluorescence from all of the six oil samples simultaneously at 5 ns-wide time-gates. (3) By implementing an interface that temporarily stores the intermingled data from the oils into a single array. The single array has two coordinates ($\lambda$, I), where $\lambda$ represents the wavelengths and I represents the measured fluorescence intensities. However, for each wavelength value there are six different fluorescence intensity values representing the six simultaneously excited oil samples. (4) By repeating steps (1), (2) and (3) using three other 5 ns-wide time-gates to produce three more time-resolved composite single arrays. Finally (5) by sorting each of the four arrays into six different TRLIF spectra, normalizing the intensities of these spectra at an arbitrary wavelength, which is chosen to correspond to the maximum intensity on of the target oil's spectra, performing spectral subtractions between the TRLIF spectra of the targeted oil sample and those of the five standard oil samples, and plotting the spectral subtractions as functions of emission wavelength and time-gate, simultaneously.

Because there are five fingerprints for each targeted oil sample, and because these five fingerprints are always referenced to some standard oil samples, these fingerprints will remain unique to this targeted oil sample as long as the same standard oil samples are always used. The advantage here is that instead of relying on only single fingerprints when discriminating between oil samples, we now have a set of five fingerprints that will do the job. Moreover, the fact that the multiple fingerprints are plotted in terms of wavelength-resolved spectral subtractions of the fluorescence intensities rather than mere time-resolved fluorescence intensities, the fingerprints provide very high distinguishing ability that is much robust than the type produced by the previous invention. The multiple fingerprints can be used (1) to discriminate between very closely similar neat crude petroleum oils, (2) to discriminate between naturally weathered spilled crude oils in seawater, (3) to identify the original grade of the an already weathered spilled crude oil in seawater if a data bank of fingerprints is available, (4) to identify the duration by which a particular crude oil has been spilled in seawater if its original grade has been identified, (5) to provide highly personalized fingerprints of crude petroleum oils as well as their thermal cuts and derivatives, and also of complex chemical mixtures in general.

Advantageously, the invention does not rely on absolute intensity measurements of the fluorescence spectra, or on any specific sample preparation procedure. Also, it does not resort to performing any de-convolution analysis; on the contrary it uses the convolution that is occurring between the laser and the resulting fluorescence pulses at the narrow time-gates as input data for the fingerprints. All of this makes this invention applicable also in remote sensing measurements.

The invention could be used also to provide near real-time fingerprints if a gated ICCD detection system is used as the data acquisition instead of the monochromator/photomultiplier/signal-processor combination.

BRIEF DESCRIPTION OF THE DRAWINGS

FIGS. 12A through 12E are charts showing the multiple fingerprints of the X2 oil (a mixture of 5% Light oil and 95% Extra Light neat oils).

FIG. 12F is a chart showing the single fingerprint of the X2 oil sample when produced using the previous invention.

DETAILED DESCRIPTION OF THE DETAILED EMBODIMENTS

The present invention is based on time-resolved laser-induced fluorescence spectroscopy and produces multiple fingerprints for any petroleum oil sample. The fingerprints are constructed from spectral subtractions between the normalized TRLIF spectra of the targeted oil sample and those of five other standard oil samples. The excitation, detection, and subtraction of the spectra are done simultaneously for the six samples at narrow time-gates; one time-gate at a time. The time-gates are four consecutive 5 ns-wide slices of the total temporal profile of the standard oils. The technique depends on the shapes of the subtracted spectra but not on their relative intensities and the produced fingerprints are of high distinguishing ability since they highlight the variations of these shapes relative to those of standard oil samples.

A detailed description of the technique is presented in remote and non-remote setups, along with an example showing how to construct the fingerprints for a particular petroleum oil sample. Additional examples of fingerprints for weathered and neat petroleum oils are also given to demonstrate the distinguishing ability of the technique in discriminating between two closely similar neat crude oils, between weathered crude oils having originally lighter grades, and between two weathered crude oils having originally heavier grades. A comparison with the single fingerprints produced by the previous invention is also presented.

Apparatus and System

The system can be built up to function in remote sensing and in non-remote sensing applications.

Figure 1:
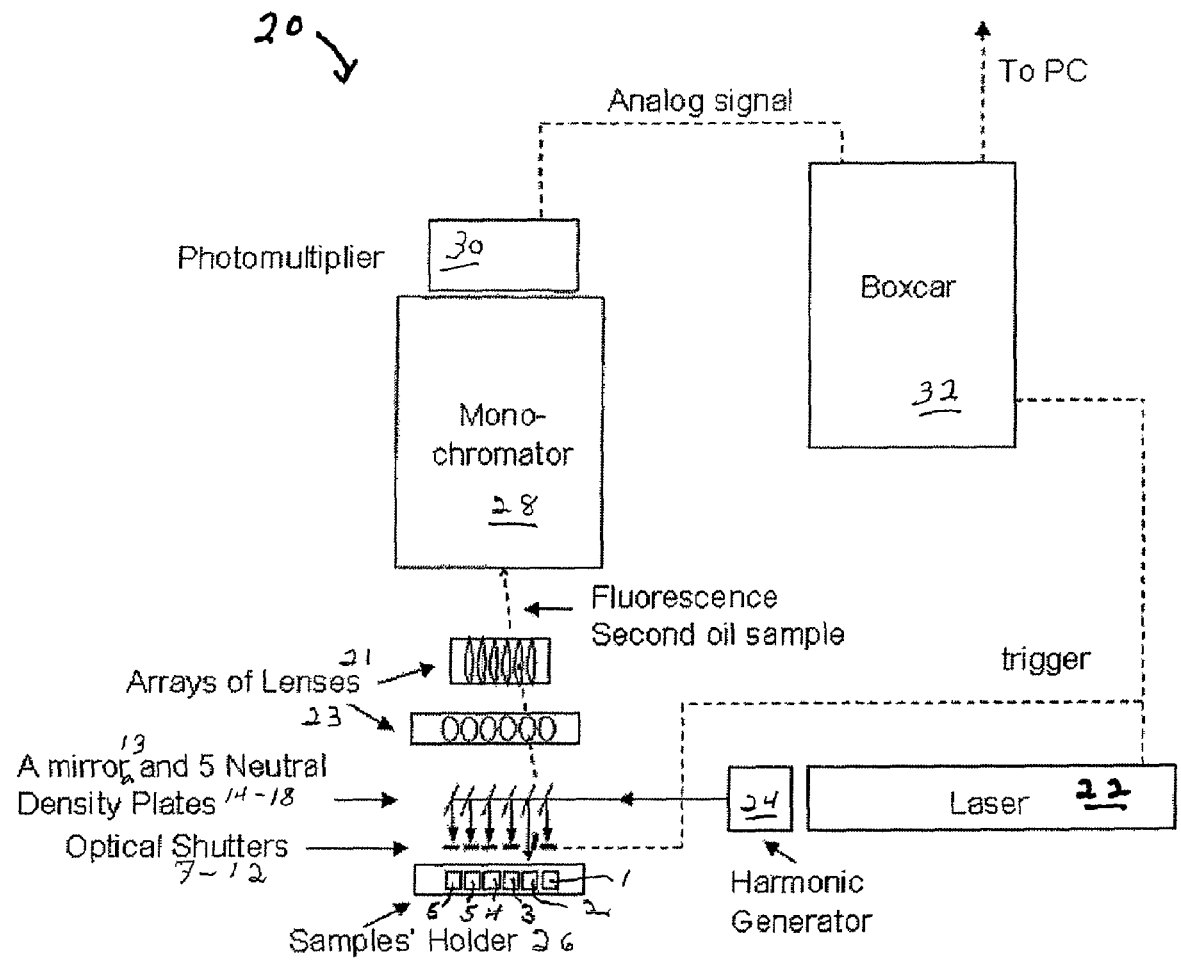
FIG. 1 is a schematic diagram for a non-remote setup. The laser-harmonic generator combination is one that produces pulsed UV radiation with wavelength at 355 nm or below. The oil samples are held inside the samples' holder. The mirror, the 5 neutral density plates and the optical shutters direct the laser beam onto one oil sample at a time. The two arrays of lenses focus the resulting fluorescence from the oil samples onto the monochromator's slit. The boxcar consists of a signal processor and a signal integrator. The monochromator-photomultiplier-boxcar combination can be replaced by a gated ICCD system. In this case the resulting fluorescence would be focused onto the ICCD camera which would act as a spectral dispersion instrument, a detector, and a boxcar.
Figure 2:
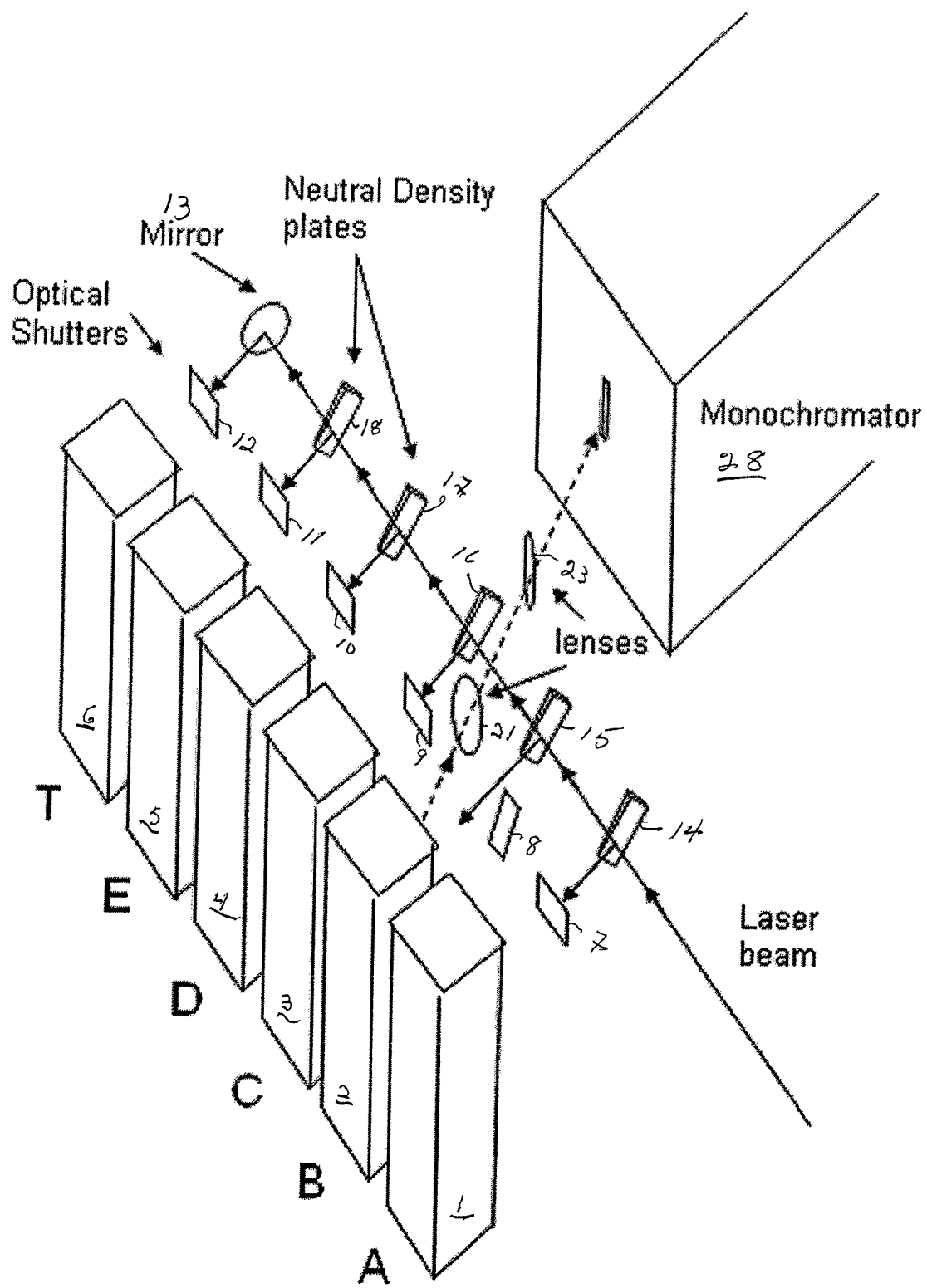
FIG. 2 is a schematic diagram of the samples' holder and the laser beam steering mechanism. The oils are held inside six identical quartz cuvettes arranged in a linear configuration. Cuvettes A through E contain the standard oil samples, while cuvette T is reserved for the targeted oil sample or specimen. The mirror and the UV density plates reflect intensity portions of the laser beam toward the oil samples at exactly the same angles. The optical shutters consist of six identical swing arms connected to six electronically-controlled stepper motors that allow the beam to pass through them one at a time. The diagram shows the moment at which only the second shutter is open. The two lenses shown are quartz lenses needed to steer the resulting fluorescence from the second oil sample onto the monochromator's slit. There are another 5 pairs of quartz lenses which are not shown.

Referring to FIG. 1, and FIG. 2 non-remote system 20 consists of a pulsed UV laser 22 with frequency doubling crystal or harmonic generator 24 to produce output at 355 nm or below, a sample holder 26 designed to hold six 1-cm square quartz cuvettes 1-6 containing the oil samples, five UV neutral density plates 14-18, one UV 100% reflecting mirror 13, six small arm shutters 7-12 with independent stepper motors controlled by an electronic circuit, two groups 21 and 23 of six quartz lenses for focusing the resulting fluorescence, a low resolution scanning monochromator 28, fast photomultiplier 30, a boxcar 32 consisting of a signal processor/integrator, and a personal computer. In the original experiments the following equipment were used: The third and fourth harmonics of Spectra Physics DCR YAG laser at wavelengths of 355-nm and 266-nm (pulse width of 6 and 8 ns, energy of ~25 mJ per pulse, and repetition rate of 10 hz), an f/3.4 Applied Physics monochromator (slit width of 1.5 mm and scanning rate of 1.6 nm/s), Hamamatsu R1564U-07 photomultiplier, A Eg&G Model 4402 signal processor, coupled with a EG&G Model 4422 gated integrator.

A description of how the system works is presented here. Referring to FIG. 2, pulses of a laser beam, running parallel to the sample holder, is crossed by five small UV neutral density plates and one 100% UV reflective mirror that deflect portions of the laser beam intensity onto the five standard oil samples and the targeted oil sample, respectively. Six small optical shutters are positioned in front of the six cuvettes and are synchronized in such a way that they allow only one cuvette to be irradiated at a time. The synchronization is done by a simple electronic circuit having the Q-switch pulse as a triggering pulse. Each shutter consists of a swing arm connected to a small stepper motor allowing the arm to rotate a quarter of a revolution in clockwise and counterclockwise directions to block and unblock the secondary laser beam, respectively. The angular speed of the shutters is 0.167 rev/s. All of the six secondary laser beams irradiate the corresponding oil samples at exactly the same angle. The shutters are designed to remain open for only 1 second through which 10 laser pulses pass through them at a time.

The resulting fluorescence pulses, emitted from the oil samples, are directed onto a 1.5-mm slit of a monochromator by means of six pairs of small quartz lenses. The monochromator is scanned in step mode, with a 6-second delay between consecutive increments. During each of the 6-second period the photomultiplier detects 60 fluorescence pulses at that particular wavelength setting of the monochromator; 10 pulses of which correspond to each of the oil samples. The detected intensities are digitized, time-resolved, and temporarily stored as six successive points in one array using a signal processor boxcar. The process is repeated for the next wavelength increment of the monochromator, adding a second group of six successive points in the signal processor array, and so on until the desired wavelength range has been scanned. The whole process is done at a fixed 5 ns-wide time-gate of the fluorescence-pulse's temporal profile, and is then repeated at three other adjacent 5 ns-wide time-gates. For each of the four time-gates, the array that is temporarily stored in the signal processor ends having six intermingled TRLIF spectra corresponding to the six oil samples. A numerical analysis procedure is then applied to sort out the six spectra, normalize them in intensity, and then perform spectral subtraction between the targeted oil sample and each of the reference samples. The end result is a group of five subtracted spectra that have been time-resolved at the first time-gate which, for simplicity, are denoted as AT1, BT1, CT1, DT1, and ET1. Where AT, BT, CT, DT, and ET refer to the targeted oil (T) normalized spectrum being subtracted from those of the A, B, C, D, and E standard oils, respectively, and the suffix 1 refers to the first 5-ns time-gate.

Each of the other three time-gates produces also a set of five normalized subtracted spectra denoted in a similar manner as (AT2, BT2, CT2, DT2, ET2), (AT3, BT3, CT3, DT3, ET3), and (AT4, BT4, CT4, DT4, ET4) for the second, third, and fourth 5-ns time-gates, respectively. Finally the desired five normalized spectral subtraction fingerprints of the targeted oil sample are produced after regrouping these spectra as sets of (AT1, AT2, AT3, AT4), (BT1, BT2, BT3, BT4), (CT1, CT2, CT3, CT4), (DT1, DT2, DT3, DT4), and (ET1, ET2, ET3, ET4), and then plotting each set in terms of a contour diagram relating the intensities of the normalized spectral subtractions to the fluorescence emission wavelength and the time-gate, simultaneously.

Figure 3:
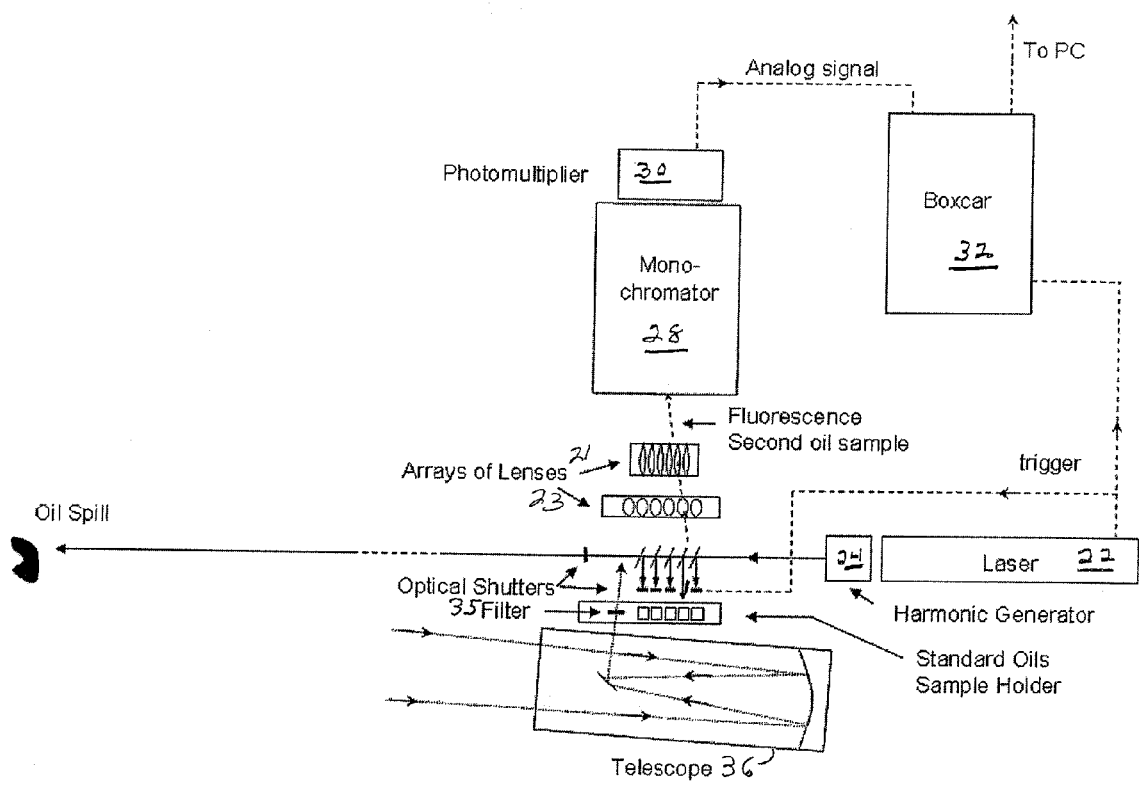
FIG. 3 is a schematic diagram for a remote sensing setup. The pulsed laser and the boxcar are described as in FIG. 1. The cuvette for the targeted oil sample is replaced by a laser filter, and the corresponding optical shutter is re-oriented in position that is perpendicular to the other 5 optical shutters. The telescope is a Newtonian telescope with a quartz eyepiece that is placed accurately in front of the laser filter. The monochromator-photomultiplier-boxcar combination can be replaced by a gated ICCD system.

The system can be constructed to work in a remote sensing mode by making only a few modifications as shown schematically in FIG. 3. The 100% UV reflecting mirror has to be removed so the laser beam can travel to the desired remote location. The samples' holder must be modified in such a way that the sixth cuvette holder is removed and is replaced by an optical filter 35 that cuts off the wavelength of the UV laser itself. A Newtonian telescope 36 must be added to the side of the samples' holder such that the eyepiece of the telescope is located exactly through the slot of the removed sixth cuvette. Also, the sixth optical shutter has to be repositioned so that it can block and unblock the beam directed at the remote location. In the data processing phase, the TRLIF spectra resulting from the targeted sample must be corrected to the spectral response of the added filter before performing the spectral subtractions.

The whole technique can be made to operate in near real-time mode, i.e., to produce instant fingerprints, if a time-gated ICCD system is used in place of the monochromator/photomultiplier/boxcar combination.

Finally, the system described here produces a set of five fingerprints for each targeted petroleum oil sample. However, it can also be modified to produce sets of fewer (or more) fingerprints by having a samples' holder of fewer (or more) slots to hold the desired number of standard oil samples.

EXAMPLES

The following examples demonstrate the procedure for constructing the multiple fingerprints for a specific targeted oil sample (Example 1), give comparisons between the multiple fingerprints of two pairs of weathered crude oils having lighter and heavier grades (Examples 2 and 3), and give comparisons between the multiple fingerprints of three closely similar neat oils (Example 4). The multiple fingerprints of the oils are also compared with the single fingerprints produced using the previous invention to show the difference between their distinguishing abilities.

The five standard oil samples in all of the following examples were chosen to be the marketed Arabian oil brands in neat conditions; namely, Super Light, Extra Light, Light, Medium, and Heavy, and they were placed in cuvettes A, B, C, D, and E respectively. The targeted oil sample was always placed in the sixth cuvette designated as T. For each targeted oil sample, and its accompanying five standard oil samples, four scans of the monochromator were made corresponding to time-resolving of the spectra at four consecutive time-gates of 5-ns width. The first time-gate always starts at the time of the maximum fluorescence response of the targeted oil sample. In examples (1), (2), and (3) the laser excitation wavelength was 355 nm and the scanning range of the monochromator was 370-700 nm, while in example (4) the corresponding parameters were 266 nm and 300-550 nm, respectively.

A weathering station was constructed to simulate natural weathering of crude oils in seawater to use them specifically in the experiments of examples (1), (2) and (3). The weathering station consisted of five basins containing 30 L of seawater each and a central steel structure with a swinging bar and paddles that simulate wave motions in the basins. An amount of 150 mL from each of the five marketed Arabian crude oils were poured on top of the seawater and were left for a total of 21 days. A small amount from each basin was collected every day and was kept in a freezer for storage until the experiments were made. During the weathering period the maximum weather temperature was 43° C. and the maximum relative humidity was 85%.

Example 1

Figure 4:
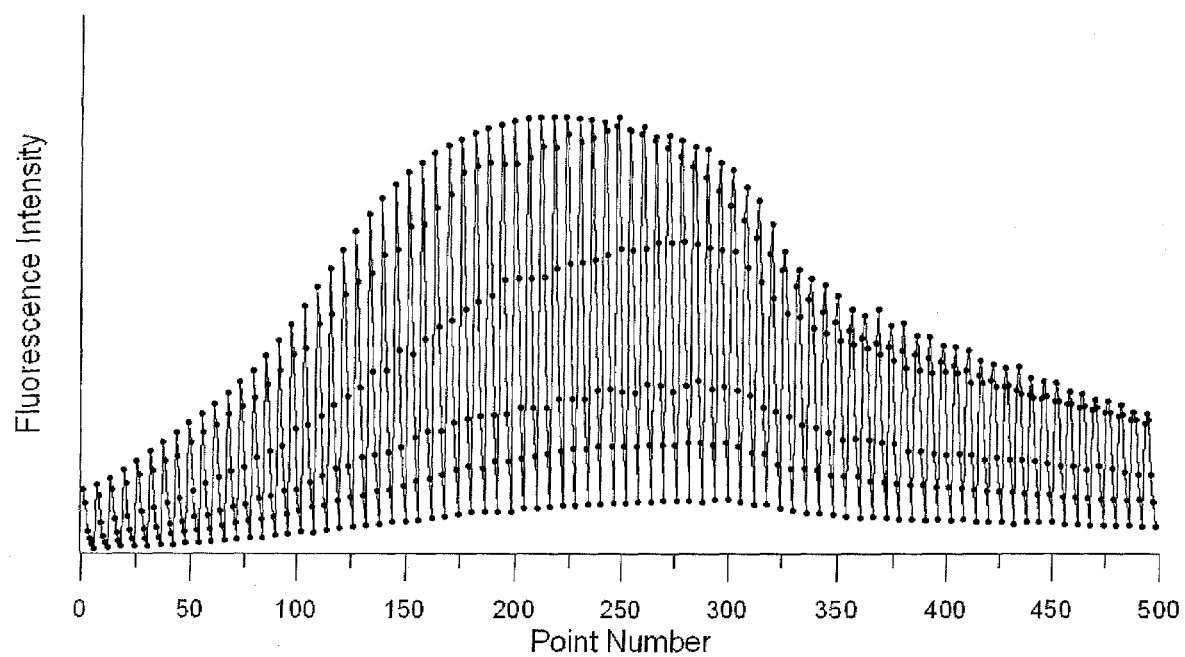
FIG. 4 is a chart showing the resulting fluorescence spectra from all of the six oil samples, intermingled with one another. Each six points on the x-axis correspond to the same wavelength setting on the monochromator. The relative intensities between the six intermingled spectra depend on the used neutral density plates and the types of oils used.

Sample and Data Analysis for Producing the Multiple Fingerprints of a Petroleum Oil Sample This example shows the type of data that is generated and analyzed by the present invention towards producing the multiple fingerprints. The targeted oil sample chosen here is some weathered oil sample having originally an "Extra Light" grade, and the laser excitation wavelength was chosen to be 355 nm. FIG. 4 shows a sample plot of the data as acquired by the signal analyzer during one scan of the monochromator.

The plot consists of groups of six successive points, each group of which is measured at a fixed wavelength setting of the monochromator, starting from 370 nm. The monochromator operated in the step mode with wavelength increment of 1.6 nm and time period of 6 s between increments. The six points in each group correspond to the six intensities of the resulting fluorescence at that particular wavelength setting. The intensities, however, are all time-resolved in the sense that only the first 5 ns time-gate of the intensities' temporal profiles has been considered in the measurements. Accordingly, the plot in FIG. 4 is one that contains six intermingled TRLIF spectra belonging to the six oil samples, all of which have been time-resolved at the first of the 5-ns time-gates.

The relative intensities of these six intermingled spectra depend on the UV neutral densities in front of each cuvette and also on the grade of the petroleum oil. However, no information will be derived from these relative intensities since the technique depends only on the shapes of the spectra.

Figure 5:
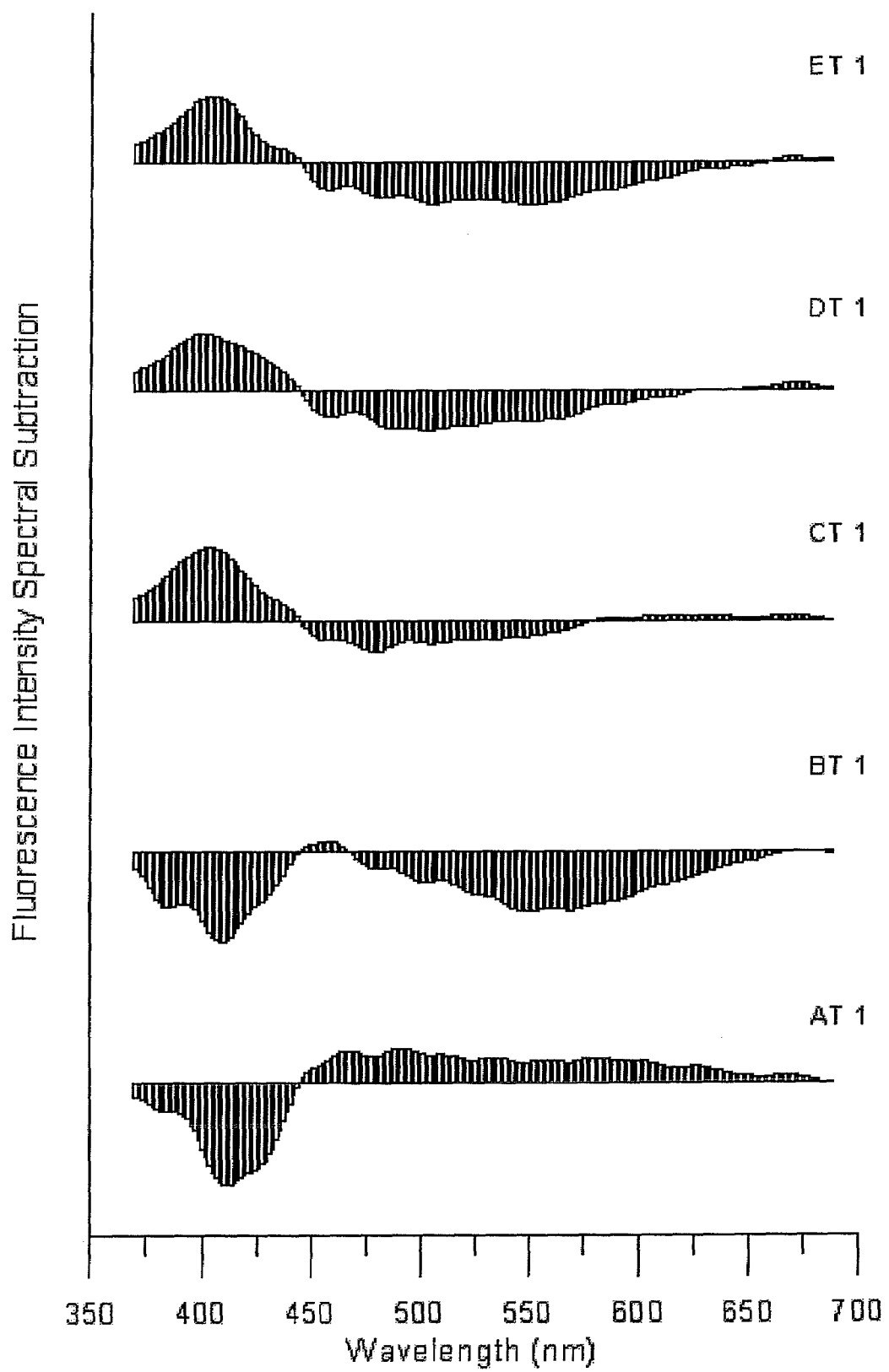
FIG. 5 is a chart showing the resulting fluorescence spectra time-resolved at the first time-gate after sorting the intermingled spectra of FIG. 4, normalizing them, and then spectrally subtracting the spectrum of targeted oil (T) from those of the standard oils (A, B, C, D, and E).

The plot in FIG. 4 represents the type of raw data acquired by, but only temporarily stored in, the signal processor. The signal processor is, in fact, programmed to output a different set of five ($\lambda$, $\Delta I$) data representing spectral subtractions between these six intermingled spectra. This is achieved by commanding the signal processor to first sort the intermingled spectrum into six individual spectra, then normalize each spectrum at a particular fluorescence emission wavelength (440 nm in this case), and finally perform the spectral subtractions between the normalized TRLIF spectrum of the targeted oil and those of the standard oil samples. FIG. 5 shows the actual outputted data from these six intermingled spectra (AT1, BT1, CT1, DT1, ET1) when plotted in terms of individual bar charts. The designations AT, BT, CT, DT, and ET refer to the normalized spectrum of the targeted oil T being subtracted from those of the A, B, C, D, and E standard oils, respectively, while the suffixes 1 refer to the time-gate being the first 5-ns time-gate.

It should be noted that each spectral subtraction chart in FIG. 5 has two distinct regions; one between 370 nm and 440 nm and the second between 440 nm and 680 nm. The creation of these two distinct regions is made arbitrarily by the choice of the wavelength at which the intensities are normalized. The intensities of the spectral subtractions in these two regions could be either positive or negative depending on the type of the standard oil in relation to the targeted oil. The first region in particular is sensitive to the grade of the oils since it gives insight about the amount of lighter aromatic compounds in the oils. If the targeted oil has a lower grade than the standard oil it is being compared to then the area in this region would necessarily be negative. If the targeted oil grade is higher than the standard oil then it is positive. This can be confirmed in FIG. 5 by noticing that the grade of the targeted oil sample, being a weathered oil of originally Extra Light, is definitely lower than those of the neat Super Light and the neat Extra Light oils, which explains why the areas in the 370-440 nm region are negative. The fact that these areas are positive in the other three cases, necessarily mean that the targeted oil is of higher grade than the neat Light, Medium, and Heavy standard oils. If the grade of the targeted oil matches that of any of the standard oil then the area in the region 370 nm 440 nm would be very close to zero. Such information can be taken advantage of in determining the grade of the weathered oil sample and also its original grade before weathering.

Data similar to the ones shown in FIG. 5 are also collected during the experiment, but at the other three adjacent 5-ns time-gates. These data would produce three additional sets of spectral subtractions that have been time-resolved at the $2^{nd}$, $3^{rd}$, and $4^{th}$ time-gates, and are designated as (AT2, BT2, CT2, DT2, ET2), (AT3, BT3, CT3, DT3, ET3), and (AT4, BT4, CT4, DT4, ET4) respectively.

Figure 6:
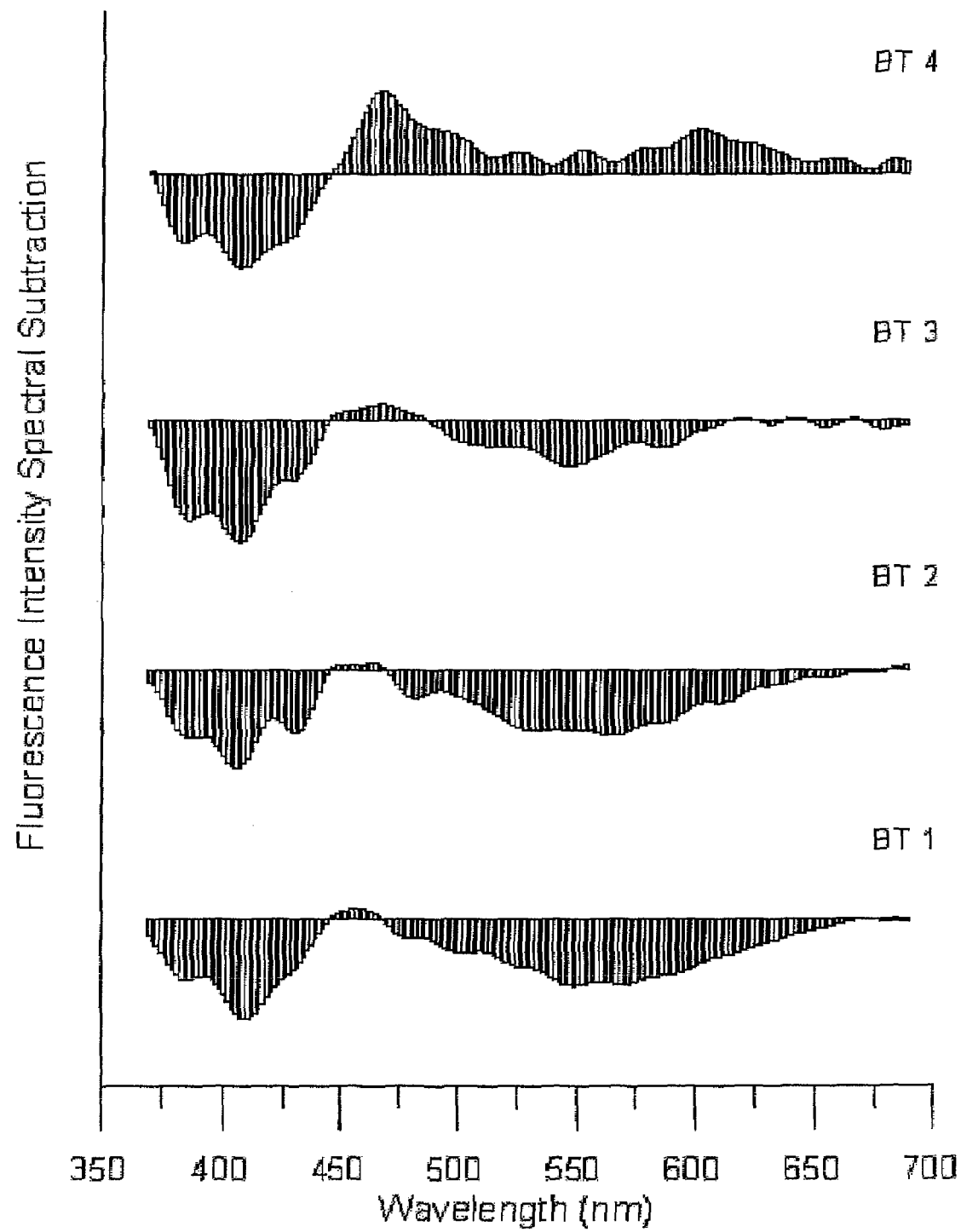
FIG. 6 is a chart showing the resulting spectral subtractions of the targeted sample (T) with respect to the second oil sample (B) at four consecutive time-gates.

Another regrouping of these spectra is taken place using PC software to present the four time-resolved spectral subtractions as five sets: (AT1, AT2, AT3, AT4), (BT1, BT2, BT3, BT4), (CT1, CT2, CT3, CT4), (DT1, DT2, DT3, DT4), and (ET1, ET2, ET3, ET4), each of which correspond to spectral subtractions with respect to one standard oil sample. FIG. 6 shows an example of one such group; namely, (BT1, BT2, BT3, BT4), which is the spectral subtractions between the normalized TRLIF spectra of the targeted oil sample and the B oil sample (neat Extra light).

The five fingerprints of the targeted oil sample are finally plotted in terms of contour diagrams relating the intensities of the subtracted spectra to the fluorescence emission wavelength and time-gate simultaneously, FIGS. 7A through 7E show the desired five fingerprints of the targeted oil sample. The single fingerprint of this targeted oil sample using the technique of the previous invention, in which the measured parameter is the non-subtracted fluorescence intensity, is shown in FIG. 7F. Hence, every single fingerprint is now being replaced by a set of five fingerprints related to five standard oils.

Example 2

Figures 7A, 7B, 7C, 7D, 7E, 7F:
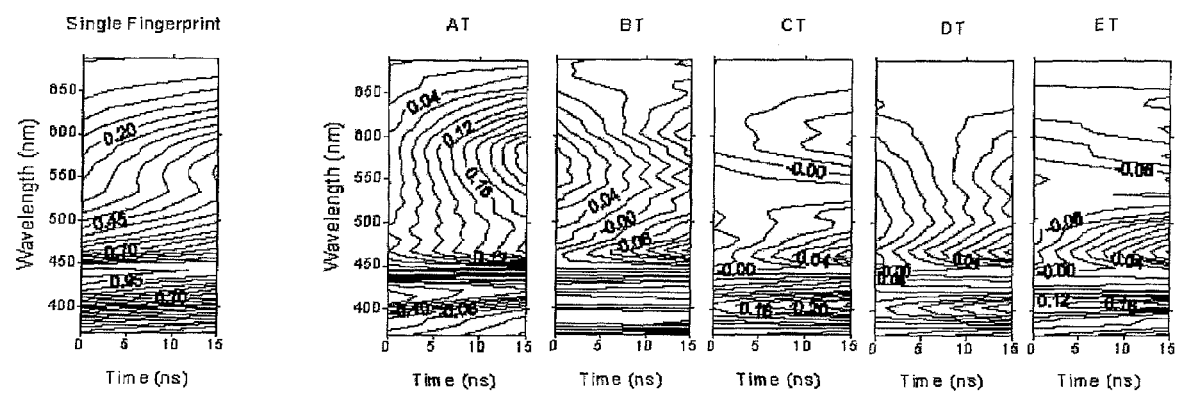
FIGS. 7A through 7E are charts showing the multiple fingerprints of the targeted oil sample in terms of contours relating the subtracted spectra to emission wavelength and time-gate, simultaneously. (The targeted oil sample is of originally Extra Light grade that had been weathered for 14-day)
FIG. 7F is a chart showing the single fingerprint of the same 14-day weathered Extra Light oil sample when produced using the previous invention.
Figures 8A, 8B, 8C, 8D, 8E, 8F:
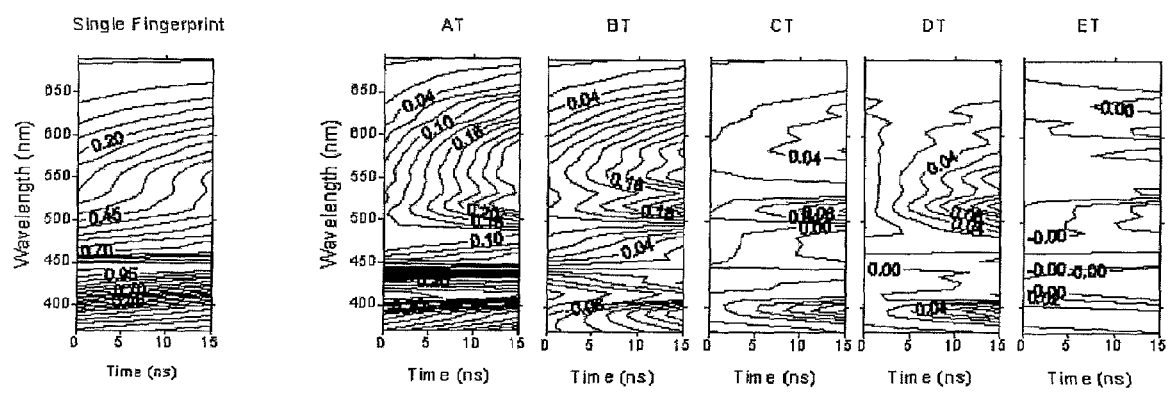
FIGS. 8A through 8E are charts showing the multiple fingerprints of an oil sample of originally Light grade that had been weathered for 14 days.
FIG. 8F is a chart showing the single fingerprint of the same 14-day weathered Light-grade oil sample when produced using the previous invention.

Comparison Between the Multiple Fingerprints of Weathered Petroleum Oils Having Originally Lighter Grades When crude oils are spilled in seawater they weather out due to evaporation, sunlight radiation, dissolving of the water soluble compounds, and due to other chemical and biological reactions. These factors change the compositional characteristics of the oils and hence change also the laser-induced fluorescence emission fingerprints. The fingerprints of weathered crude oils having originally a light grade are found to gradually turn in shape into those of heavier grades. The present example considers the case of discriminating between weathered crude oils of originally "Extra Light" and "Light" grades, which have been in the weathering station for 14 days. The multiple fingerprints that have already been shown in FIG. 7A through FIG. 7E are actually for the weathered "Extra Light" oil. The multiple fingerprints of the weathered "Light" oil, on the other hand, are presented in FIG. 8A through FIG. 8E. A quick comparison between these two sets of fingerprints would immediately establish that the two oils are different. This conclusion, on the other hand, would not have been easily reached had the comparison been made between the single fingerprints of the type produced by the previous invention. Such single fingerprints are shown in FIGS. 7F and 8F for the weathered "Extra Light" and "Light" oils, respectively. It is clear then that the distinguishing ability of the multiple fingerprints is much higher than that of the single fingerprints.

Each of the multiple fingerprints of FIGS. 7A through 7E and FIGS. 8A through 8E, there has two distinct regions in each fingerprint as mentioned above. The first is between 370 nm and 450 nm and the second is between 450 nm and 700 nm. This is resulting from the fact that there are two distinct regions in the spectral subtractions as explained above. When comparing the multiple fingerprints of the different oils patterns belonging to each region should be compared together. The first region is always useful in discriminating between oils of different grades while the second region is always useful when discriminating between oils having a similar grade. In the present example one can see that the single fingerprints of the two oil sample FIGS. 7F and 8F can barely discriminate between the grades of the oils since the patterns in the 370-440 nm region are alike. The multiple fingerprints, on the hand, lead to the conclusion that the two samples are not only different but that also the grades are different.

Example 3

Figures 9A, 9B, 9C, 9D, 9E, 9F:
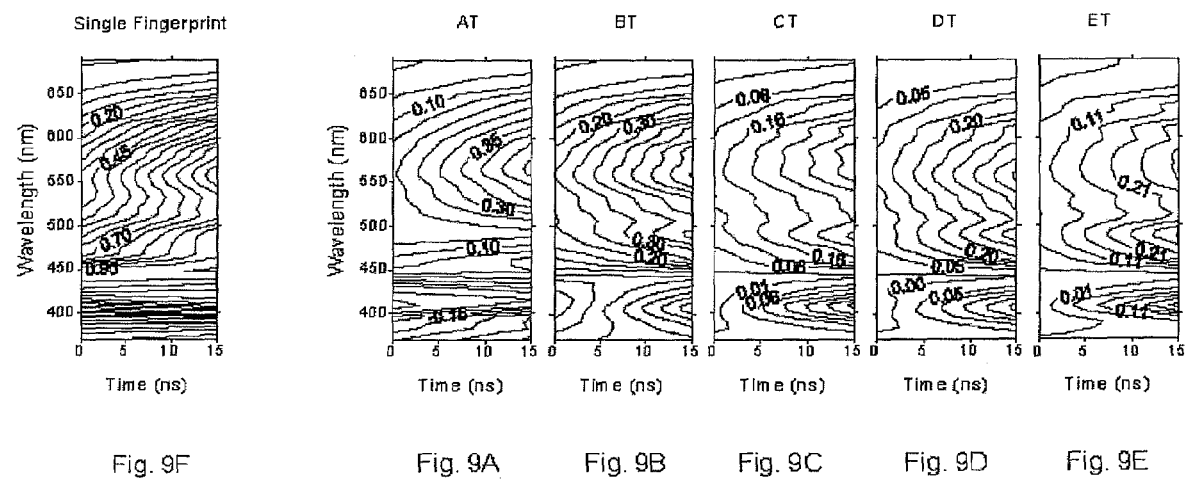
FIGS. 9A through 9E are charts showing the multiple fingerprints of an oil sample of originally Medium grade that had been weathered for 14 days.
FIG. 9F is a chart showing the single fingerprint of the same 14-day weathered Medium-grade oil sample when produced using the previous invention.
Figures 10A, 10B, 10C, 10D, 10E, 10F:
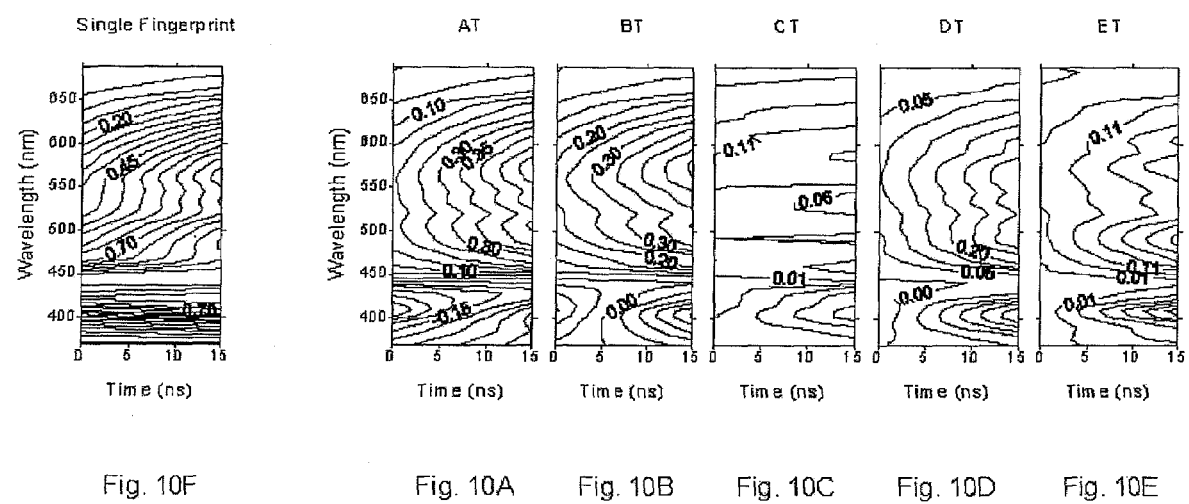
FIG. 10A through 10E are charts showing the multiple fingerprints of an oil sample of originally Heavy grade that had been weathered for 7 days.
FIG. 10F is a chart showing the single fingerprint of the same 7-day weathered Heavy-grade oil sample when produced using the previous invention.

Comparison Between the Multiple Fingerprints of Weathered Petroleum Oils Having Originally Heavier Grades In this example multiple fingerprints of weathered oils having originally "Medium" and "Heavy" grades are presented. The "Medium" oil was weathered for 14 days while the "Heavy" oil was weathered for 7 days. The single fingerprints of the two oils, i.e., the fingerprints produced by the technique of the previous invention, are shown in FIGS. 9F and 10F for the medium and heavy oils, respectively. The two oils can be somehow distinguished from each other in these fingerprints, but because the patterns in the 370 nm-450 nm region are similar in both fingerprints the oils could be mistakenly identified as originally having the same grade. However, a comparison between the multiple fingerprints of the two oils, which are shown in FIG. 9A through FIG. 9E for the medium grade, and in FIG. 10A through FIG. 10E for the heavy grade, show that the oils do originate from two different grades. This is again based on the fact that one of the multiple fingerprints, i.e., AT in FIG. 9A, has patterns that are significantly different from that of FIG. 10A. Notice also that the patterns in the region 440-680 nm in FIGS. 9A, 9B, and 9C are more contrasted with FIGS. 10A, 10B, and 10C than FIG. 9F with FIG. 10F.

Example 4

Comparison Between the Multiple Fingerprints of Closely Similar Neat Petroleum Oils The laser excitation wavelength in the previous three examples was 355 nm. In this example we use a laser wavelength of 266 nm, which can excite aromatic compounds of lighter molecular mass, and a normalization wavelength at 470 nm instead of 440 nm. The aim here is to examine the multiple fingerprints of closely similar neat crude oils instead of weathered ones. First, a set of closely similar oil mixtures were prepared by mixing known volumes of two crude oils together; namely Extra Light and Light crude oils. At start a mixture of 1% Light oil with 99% Extra Light oil was prepared and the multiple fingerprints of this mixture with those of the Extra Light oil were compared to see if they could be distinguished from each other. If not then a mixture of 2% and 98% is tried, and so on, until the two oils are satisfactorily distinguished. This limit was reached when a volume mixture of about 5% Light and 95% Extra Light oils were mixed together. For simplicity, we designate this particular oil mixture as X2 and the pure Extra Light oil as X1. A third oil mixture, designated as X3, having volume ratios of 10% Light and 90% Extra Light was also prepared for comparison reasons.

Figures 11A, 11B, 11C, 11D, 11E, 11F:
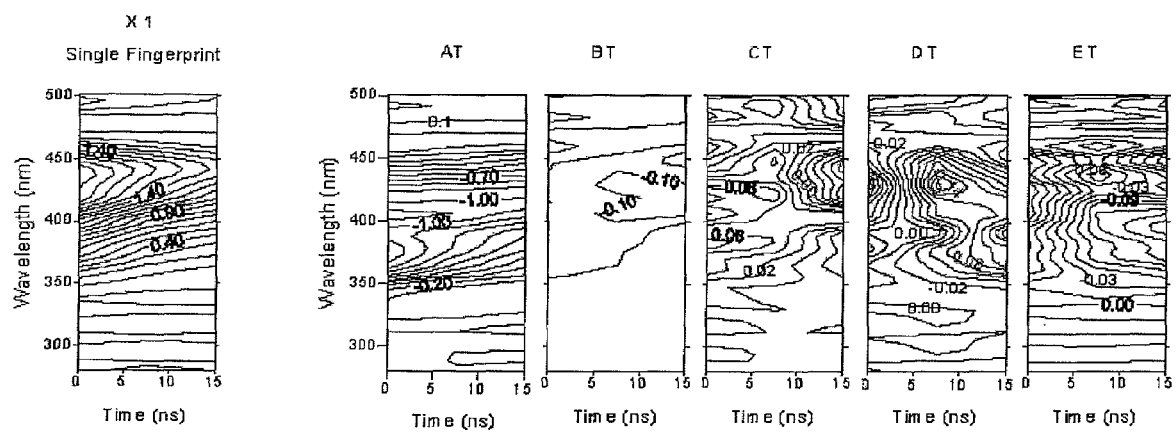
FIG. 11A through 11E are charts showing the multiple fingerprints of the X1 oil (a neat oil sample of pure Extra Light grade).
FIG. 11F is a chart showing the single fingerprint of the X1 oil sample when produced using the previous invention.
Figures 12, 12A, 12B, 12C, 12D, 12F:
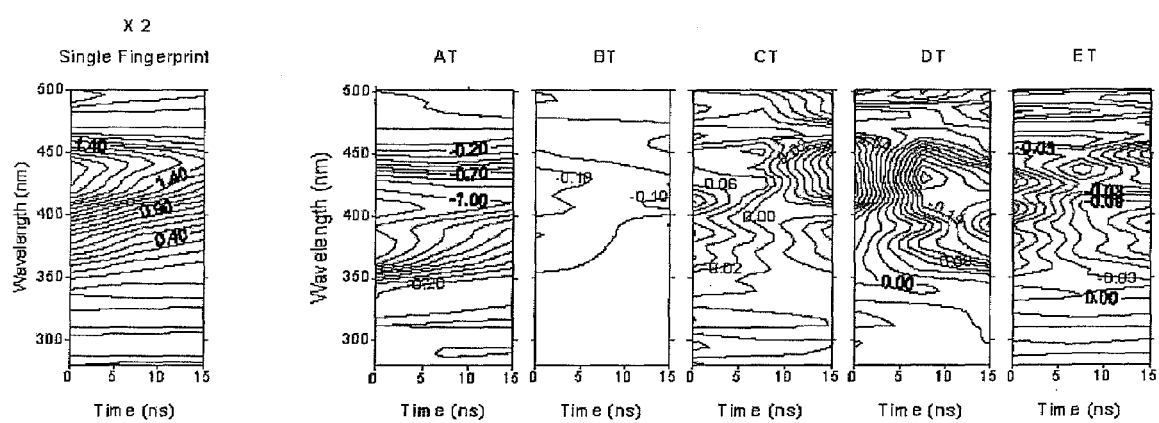
Figures 13A, 13B, 13C, 13D, 13E, 13F:
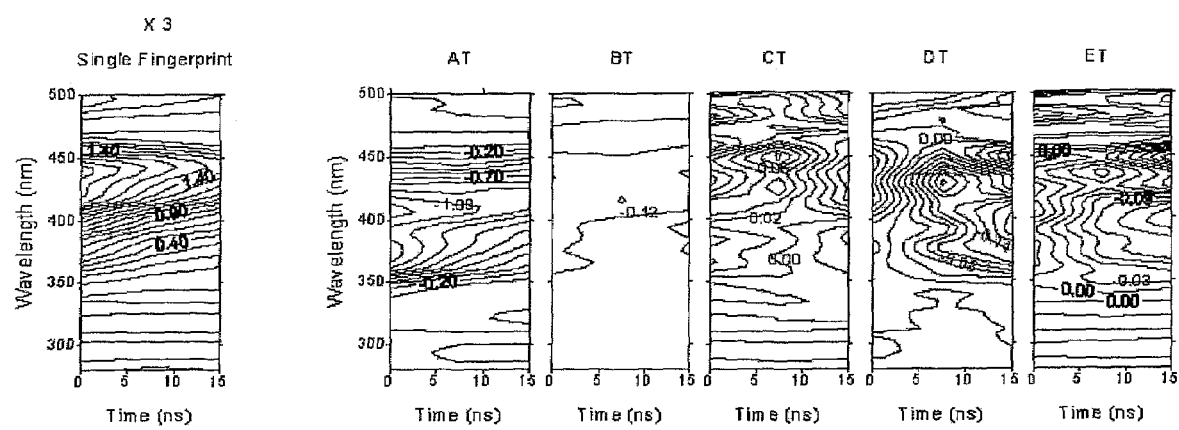
FIGS. 13A through 13E are charts showing the multiple fingerprints of the X3 oil (a mixture of 10% Light oil and 90% Extra Light neat oils).
FIG. 13F is a chart showing the single fingerprint of the X3 oil sample when produced using the previous invention.

By using the method of the previous invention it is not possible to discriminate between these particular three oil mixtures. This can be seen by comparing FIGS. 11F, 12F, and 13F corresponding to single fingerprints of the X1, X2, and X3 oils respectively. On the other hand, the multiple fingerprints of the present technique could easily distinguish between them. This can be confirmed by comparing FIGS. 11A-11E with FIGS. 12A-12E and with FIGS. 13A-13E. Notice that, because the grades of the X1, X2, and X3 oils are all close to the Extra Light grade, the patterns in the BT fingerprint for the three samples are very close to zero.

While the invention has been described in connection with its preferred embodiments, it should be recognized that changes and modifications may be made therein without departing from the scope of the appended claims.

What is claimed is:

1. A method for characterization and fingerprinting of petroleum oils using normalized time-resolved laser-induced fluorescence comprising the steps of:
    exposing an unknown petroleum oil sample to a pulse of ultraviolet laser radiation;
    simultaneously exposing a plurality of known petroleum oil samples to a pulse of ultraviolet laser radiation by a single laser;
    measuring the intensities of resulting fluorescence over the spectrum of wavelengths of light from said petroleum oil samples at specific narrow time gates of between about 2 to about 5 nanoseconds within the temporal response of said laser pulse to form a wavelength-resolved fluorescence spectrum for each of said samples;
    sorting the resulting intermingled wavelength-resolved fluorescence spectra into a plurality of individual fluorescence spectra;
    normalizing said wavelength resolved fluorescence spectrums at a particular emission wavelength;
    measuring the spectral subtractions of the known petroleum oil samples wavelength-resolved laser-induced fluorescence spectrum relative to those of the known petroleum oil samples to produce a plurality of resulting fingerprints; and
    comparing the resulting fingerprints;
    characterizing said unknown petroleum oil sample based on similarities of its resultant plots with those of said known petroleum oil sample.

2. A method of characterization and fingerprinting of petroleum oils according to claim 1, wherein the time is determined relative to the maximum temporal response of the laser pulse.

3. A method of characterization and fingerprinting of petroleum oils according to claim 2, wherein said pulse of laser radiation is in the UV region preferably shorter than or equal to 355 nm in wavelength and said normalized wavelength corresponds to the maximum intensity of the fluorescence.

4. A method of characterization and fingerprinting of petroleum oils according to claim 3, wherein the pulse of laser radiation is from four to fifteen nanoseconds.

5. A method of characterization and fingerprinting of petroleum oils according to claim 1, wherein said unknown petroleum oil sample is non-remote.

6. A method of characterization and fingerprinting of petroleum oils according to claim 1, wherein the unknown petroleum oil sample is remotely located.

7. An apparatus for the characterization and fingerprinting of oils using normalized wavelength-resolved laser-induced fluorescence comprising:
    means including a laser for generating a pulse of ultraviolet laser radiation and means including a plurality of quartz cuvettes plus 1 quartz cuvette for holding an unknown petroleum oil sample and the other cuvettes for holding the plurality of known oil samples and wherein said quartz cuvettes are arranged parallel to each other in a linear configuration for simultaneously exposing the sample of the unknown petroleum oil and the plurality of samples of known petroleum oils to a pulse of ultrasonic laser radiation;

means for measuring the intensities of resulting fluorescence over the spectrum of wavelengths of light from the petroleum oil samples at specific narrow time gates within the temporal response of the laser pulse to form a wavelength-resolved spectrum for each of said samples;

means for normalizing the wavelength-resolved spectrum at a preselected emission wavelength; and means for plotting the wavelength-resolved spectrum of said samples in contours of intensity spectral subtractions as functions of wavelength and time simultaneously to thereby characterize said unknown petroleum oil sample based on similarities to the resultant plots of said known petroleum oil samples.

8. An apparatus for the characterization and fingerprinting of oils using normalized wavelength-resolved laser-induced fluorescence according to claim 7, in which said means for generating a pulse of ultraviolet radiation includes a harmonic generator.

9. An apparatus for the characterization and fingerprinting of oils using normalized wavelength-resolved laser-induced fluorescence according to claim 8, includes 6 quartz cuvettes for holding a specimen of unknown petroleum oil and 5 samples of known petroleum oils.

10. An apparatus for the characterization of oils using normalized wavelength-resolved laser-induced fluorescence according to claim 8, in which said means for measuring the resulting fluorescence is a monochromator.

11. An apparatus for the characterization of oils using normalized wavelength-resolved laser-induced fluorescence according to claim 10, which includes a plurality of quartz lenses for focusing resulting fluorescence pulses from the test specimen and plurality of samples on said monochromator.

12. An apparatus for the characterization and fingerprinting of oils using normalized wavelength-resolved laser-induced fluorescence according to claim 11, which includes an electronic timer circuit, a plurality of stepper motors and a plurality of optical shutters mounted on said stepper motor and controlled by said electronic timer circuit to block and unblock a secondary laser beam.

13. An apparatus for producing a set of multiple fingerprints of petroleum oils using normalized wavelength-resolved laser-induced fluorescence spectral subtractions comprising a laser and a harmonic generator for producing pulse ultraviolet radiation, a plurality of sample holders for holding a test specimen of an unknown petroleum oil and a plurality of samples of known petroleum oils, a plurality of neutral density plates and a UV reflecting mirror for directing pulsed ultraviolet radiation onto said specimen and each of said plurality of samples one at a time, an electronic timer circuit, a plurality of stepper motors and a plurality of optical shutters mounted on said stepper motors and controlled by said electronic timer circuit to block and unblock a secondary laser beam, a monochromator including a slit and a plurality of lenses focusing the resulting fluorescence pulses from the test specimen and plurality of samples on said slit, a computer and a box car including a signal processor and a signal integrator for producing a signal and (spectral subtractions) sending the signal to said computer for producing multiple fingerprints of said test specimen and said plurality of samples.

14. An apparatus for producing a set of multiple fingerprints of petroleum oils using normalized wavelength-resolved laser-induced fluorescence spectral subtractions in accordance with claim 13, wherein said sample holders are quartz cuvettes and said lenses are quartz lenses.

* * * * *